(12) United States Patent
Harlev et al.

(10) Patent No.: US 12,096,976 B2
(45) Date of Patent: Sep. 24, 2024

(54) ABLATION ENERGY CONTROLLING

(71) Applicant: Affera, Inc., Watertown, MA (US)

(72) Inventors: Doron Harlev, Watertown, MA (US); Paul B. Hultz, Watertown, MA (US); Robert Alan Mest, Watertown, MA (US)

(73) Assignee: AFFERA, INC., Watertown, MA (US)

( * ) Notice: Subject to any disclaimer, the term of this patent is extended or adjusted under 35 U.S.C. 154(b) by 163 days.

(21) Appl. No.: 16/761,237

(22) PCT Filed: Nov. 26, 2018

(86) PCT No.: PCT/US2018/062460
§ 371 (c)(1),
(2) Date: May 1, 2020

(87) PCT Pub. No.: WO2019/108479
PCT Pub. Date: Jun. 6, 2019

(65) Prior Publication Data
US 2020/0360079 A1   Nov. 19, 2020

Related U.S. Application Data

(60) Provisional application No. 62/592,841, filed on Nov. 30, 2017.

(51) Int. Cl.
*A61B 18/14* (2006.01)
*A61B 18/00* (2006.01)
(Continued)

(52) U.S. Cl.
CPC ...... *A61B 18/1492* (2013.01); *A61B 18/1206* (2013.01); *A61B 18/16* (2013.01);
(Continued)

(58) Field of Classification Search
CPC . A61B 18/1492; A61B 18/1206; A61B 18/16; A61B 2018/00577;
(Continued)

(56) References Cited

U.S. PATENT DOCUMENTS 3,683,923 A   8/1972   Anderson
4,657,015 A   4/1987   Irnich
(Continued)

FOREIGN PATENT DOCUMENTS

DE   19717411 A1   11/1998
WO   2018165425 A1   9/2018
WO   2019108479 A1   6/2019

OTHER PUBLICATIONS

ISA, "PCT Application No. PCT/US18/21545, International Search Report and Written Opinion mailed Jun. 18, 2018", 18 pages.
(Continued)

*Primary Examiner* — Khadijeh A Vahdat
*Assistant Examiner* — Abigail M Ziegler
(74) *Attorney, Agent, or Firm* — Tarolli, Sundheim, Covell & Tummino LLP

(57) ABSTRACT

Devices, systems, and methods of the present disclosure are directed to selectively controlling delivery of electrical energy to an ablation electrode, with the selective control based on a history of the electrical energy delivered to a return electrode (e.g., electrical energy delivered in a current time-step and in one or more time-steps preceding the current time-step). Controlling electrical energy delivered to an ablation electrode based on the history of electrical energy delivered to a return electrode can reduce the likelihood of unintended tissue damage away from a treatment site as electrical energy is delivered to the treatment site via the ablation electrode. Further, or instead, the devices, systems, and methods of the present disclosure can reduce
(Continued)

the likelihood of unintended tissue damage away from the treatment site while reducing or eliminating the need to interrupt lesion formation by the ablation electrode.

20 Claims, 8 Drawing Sheets

(51) Int. Cl.
    *A61B 18/12*     (2006.01)
    *A61B 18/16*     (2006.01)

(52) U.S. Cl.
    CPC ............... *A61B 2018/00577* (2013.01); *A61B 2018/00702* (2013.01); *A61B 2018/0072* (2013.01); *A61B 2018/00761* (2013.01); *A61B 2018/00779* (2013.01); *A61B 2018/165* (2013.01); *A61B 2018/167* (2013.01)

(58) Field of Classification Search
    CPC .. A61B 2018/00702; A61B 2018/0072; A61B 2018/00761; A61B 2018/162; A61B 2018/165; G06F 3/048
    See application file for complete search history.

(56) References Cited

U.S. PATENT DOCUMENTS

| | | | |
|---|---|---|---|
| 5,277,201 A | | 1/1994 | Stern |
| 5,423,808 A | | 6/1995 | Edwards et al. |
| 5,573,533 A | | 11/1996 | Strul |
| 5,827,276 A | | 10/1998 | LeVeen et al. |
| 6,139,546 A | | 10/2000 | Koenig et al. |
| 6,190,381 B1 | | 2/2001 | Olsen et al. |
| 6,258,085 B1 | * | 7/2001 | Eggleston .......... A61B 18/1233 606/42 |
| 6,319,249 B1 | | 11/2001 | Tollner |
| 6,740,080 B2 | | 5/2004 | Jain et al. |
| 7,736,359 B2 | * | 6/2010 | McPherson ........ A61B 18/1233 606/35 |
| 7,879,029 B2 | | 2/2011 | Jimenez |
| 8,364,237 B2 | | 1/2013 | Stone et al. |
| 8,449,536 B2 | | 5/2013 | Selig |
| 11,147,618 B2 | * | 10/2021 | Gearheart .......... A61B 18/1206 |
| 11,490,958 B2 | | 11/2022 | Harlev et al. |
| 2004/0206365 A1 | | 10/2004 | Knowlton |
| 2005/0101947 A1 | | 5/2005 | Jarrard et al. |
| 2005/0113817 A1 | * | 5/2005 | Isaacson ................ A61B 18/16 606/34 |
| 2007/0049919 A1 | | 3/2007 | Lee et al. |
| 2007/0167942 A1 | | 7/2007 | Rick |
| 2008/0051777 A1 | | 2/2008 | Haemmerich |
| 2008/0071263 A1 | | 3/2008 | Blaha |
| 2009/0036884 A1 | | 2/2009 | Gregg et al. |
| 2009/0187183 A1 | | 7/2009 | Epstein |
| 2013/0138097 A1 | * | 5/2013 | Mathur .............. A61B 18/1233 606/35 |
| 2013/0165919 A1 | | 6/2013 | Epstein |
| 2015/0182278 A1 | * | 7/2015 | Ehninger ........... A61B 18/1233 606/34 |
| 2015/0320478 A1 | * | 11/2015 | Cosman, Jr. ........... A61B 18/16 606/34 |
| 2016/0038216 A1 | * | 2/2016 | Woo ....................... A61B 90/04 606/34 |

OTHER PUBLICATIONS

ISA, "PCT Application No. PCT/US18/62460, International Search Report and Written Opinion mailed Mar. 14, 2019", 17 pages.
Division of Technical Resources—Office of Research Facilities, "Closed Transition Automatic Transfer Switch", Sep. 2016, National Institutes of Health, Issue 56 (Year: 2016).

* cited by examiner

ABLATION ENERGY CONTROLLING

CROSS REFERENCE TO RELATED APPLICATIONS

The present application is a 35 U.S.C. § 371 U.S. National Phase application of International Application No. PCT/US2018/062460, filed Nov. 26, 2018, which claims the benefit of U.S. Provisional Patent Application No. 62/592,841, filed Nov. 30, 2017, both of which are incorporated herein by reference in their entireties.

BACKGROUND

Catheters are used to deliver electrical energy to tissue as part of a variety of procedures related to treatment of medical conditions in patients. In certain applications, return electrodes can be placed on skin of the patient to serve as respective return paths for the electrical energy delivered by an ablation electrode to a treatment site. However, at certain levels, the electrical energy moving through each return electrode can damage tissue away from the treatment site. Accordingly, there remains a need to control electrical energy moving through the return electrodes positioned on skin of the patient during certain types of medical treatments and, in particular, those medical treatments including tissue ablation.

BRIEF DESCRIPTION OF THE DRAWINGS

The disclosure will be understood more fully from the detailed description given below and from the accompanying drawings of various implementations of the disclosure. The drawings, however, should not be taken to limit the disclosure to the specific implementations, but are for explanation and understanding only. Like reference symbols in the various drawings indicate like elements.

DETAILED DESCRIPTION

A. Overview

Figure 1:
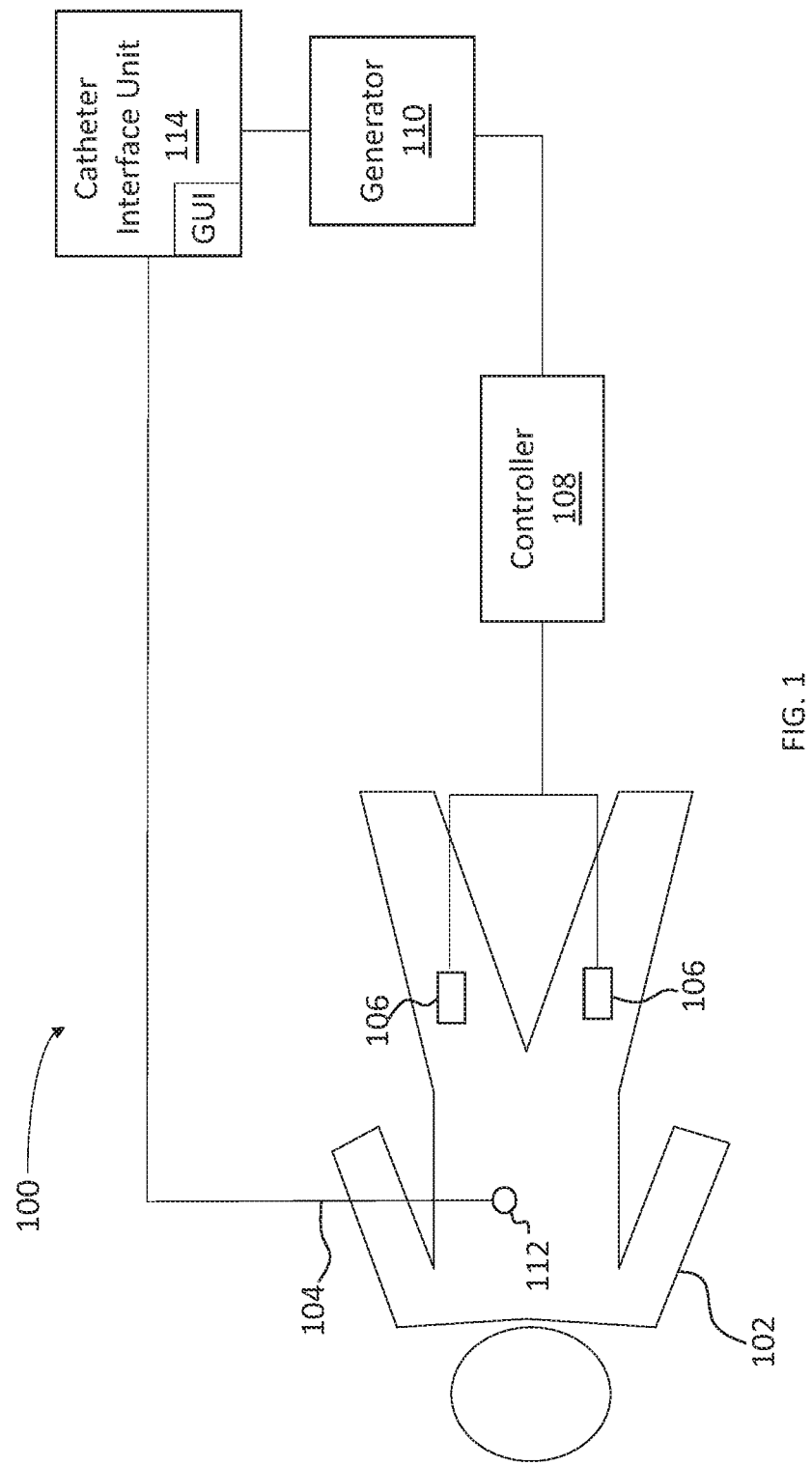
FIG. 1 is a schematic representation of a tissue ablation system.

The present disclosure is generally directed to devices, systems, and methods of delivering ablation energy to an anatomic structure of a patient in any one or more of various different medical procedures in which ablation energy is delivered to tissue at a treatment site within a patient and returns to a plurality of return electrodes on skin of the patient. In particular, devices, systems, and methods of the present disclosure are directed to selectively controlling delivery of electrical energy to an ablation electrode, with the selective control based on a history of the electrical energy delivered to a return electrode (e.g., electrical energy delivered in a current time-step and in one or more time-steps preceding the current time-step). Controlling electrical energy delivered to an ablation electrode based on the history of electrical energy delivered to a return electrode can reduce the likelihood of unintended tissue damage away from a treatment site as electrical energy is delivered to the treatment site via the ablation electrode. Further, or instead, the devices, systems, and methods of the present disclosure can reduce the likelihood of unintended tissue damage away from the treatment site while reducing or eliminating the need to interrupt lesion formation by the ablation electrode.

For the sake of clarity of explanation, the devices, systems, and methods of the present disclosure are described in the context of cardiac ablation procedures. However, unless otherwise specified or made clear from the context, the devices, systems, and methods of the present disclosure should be understood to be generally additionally, or alternatively, applicable to medical procedures in which an ablation electrode is positioned within a patient and a plurality of return electrodes are positioned on skin of the patient. By way of example, and not limitation, such medical procedures can include ablating tumors in cancer treatment and electro-surgery procedures in which tissue is cut and substantially simultaneously cauterized to avoid or minimize bleeding.

As used herein, the term "electrode" shall be understood to include an electrically conductive material used to make contact with a nonmetallic part (e.g., skin, tissue, blood, irrigation fluid, and combinations thereof) of an electrical circuit formed as energy is delivered to a treatment site as part of a medical procedure. Thus, more specifically, the term "ablation electrode" shall be understood to include an electrically conductive portion of a catheter for delivery of electrical energy to a treatment site through direct and/or indirect contact between the ablation electrode and the treatment site. Further, or instead, the term "return electrode" shall be understood to include an electrode forming a return path for at least a portion of electrical energy delivered by the ablation electrode to the treatment site.

Certain details are set forth in the following description and in FIGS. 1-8 to provide a thorough understanding of various implementations of the disclosure. Other details describing well-known structures and systems often associated with ablation electrodes and associated systems and methods, however, are not set forth below to avoid unnecessarily obscuring the description of various implementations of the disclosure.

Many of the details, dimensions, angles, and other features shown in FIGS. 1-8 are merely illustrative of particular implementations. Accordingly, other implementations can have other details, dimensions, angles, and features without departing from the spirit or scope of the present disclosure. In addition, those of ordinary skill in the art will appreciate that further implementations of the disclosure can be practiced without several of the details described below.

B. Selected Implementations of Controlling Ablation Energy and Related Devices, Systems, and Methods FIG. 1 is a schematic representation of a tissue ablation system 100 during an ablation treatment being performed on a patient 102. The tissue ablation system 100 can include a catheter 104, return electrodes 106, a controller 108, and a generator 110 in electrical communication with one another. The catheter 104 includes an ablation electrode 112 and, in use, the ablation electrode 112 is positioned in contact with tissue in an anatomic structure (e.g., a heart chamber) of the patient 102. Electrical energy from the generator 110 is delivered from the ablation electrode 112 to the tissue, a portion of the electrical energy moves from the tissue of the anatomic chamber of the patient 102 to the return electrodes 106 positioned on skin of the patient 102, and, ultimately, at least some of the electrical energy returns to the generator 110 to complete the circuit formed by the tissue ablation system 100. As described in greater detail below, the controller 108 controls distribution of the electrical energy among the return electrodes 106 in a fixed position in contact with skin of the patient 102. Accordingly, the controller 108 can reduce or eliminate the need to reposition the return electrodes 106 to maintain a desired distribution of electrical energy through the return electrodes 106 during a medical treatment.

In general, the catheter 104 can be intravascularly deliverable to a treatment site (e.g., through insertion in a femoral artery), where the ablation electrode 112 can be positioned relative to tissue at a treatment site. For example, the ablation electrode 112 can be expandable (e.g., self-expandable and/or balloon expandable) or non-expandable for positioning relative to tissue at the treatment site. While such positioning and treatment of tissue through the delivery of electrical energy from the ablation electrode 112 to the tissue can be associated with any one or more of various different medical procedures, the tissue ablation system 100 is herein described in the context of ablating cardiac tissue. For example, the ablation electrode 112 can be positioned in contact with tissue in a heart chamber of the patient 102 such that electrical ablation energy is delivered from the ablation electrode 112 to targeted tissue to form one or more lesions. The one or more lesions can be useful, for example, for interrupting electrical patterns associated with cardiac arrhythmia. Additionally, or alternatively, while the ablation electrode 112 is described as a single electrode, it should be appreciated that the ablation electrode 112 can be a plurality of ablation electrodes.

The generator 110 can drive electrical energy from the ablation electrode 112 to the return electrodes 106. The electrical energy driven by the generator 110 can be sufficient for ablating tissue in proximity to the ablation electrode 112 during a medical treatment. For example, the generator 110 can be a radiofrequency (RF) energy generator (e.g., any one or more RF energy generators well known in the art) such that the ablation energy delivered by the ablation electrode 112 to the tissue can be RF energy (e.g., in the range of 350-500 kHz). Additionally, or alternatively, the generator 110 can generate electrical energy in other frequency ranges (e.g., microwave or a set of electroporation pulses) suitable for medical treatment.

In certain implementations, the tissue ablation system 100 can additionally, or alternatively, include a catheter interface unit 114 in electrical communication (e.g., wired electrical communication) with the generator 110 and the catheter 104. The catheter interface unit 114 can include, for example, a graphical user interface to display information (e.g., positional information) about the ablation electrode 112 during treatment. Further, or instead, the catheter interface unit 114 can display information about the electrical energy driven between the ablation electrode 112 and the return electrodes 106 by the generator 110. As a specific example, the catheter interface unit 114 can display information related to whether the tissue ablation system 100 is in a therapy mode and, more specifically, information related to a duration of lesion formation.

The return electrodes 106 can be positionable on skin of the patient. For example, each one of the return electrodes 106 can be secured in a fixed position on the skin of the patient such that the return electrodes 106 remain in place when subjected to incidental forces, as may be experienced, for example, during repositioning of the patient 102 during the treatment. In certain implementations, each of the return electrodes 106 can include an adhesive surface such that the respective one of the return electrodes 106 can be releasably secured to skin of the patient 102 by placing the adhesive surface in contact with skin of the patient 102.

The return electrodes 106 can be releasably securable to skin of the patient 102 in a configuration in which the return electrodes 106 are spaced apart from one another (e.g., with one of the return electrodes 106 on the back of the patient 102 and another one of the return electrodes 106 on a leg of the patient 102). While the return electrodes 106 are described as including two electrodes, it should be understood that additional return electrodes 106 can be used. For example, the number of the return electrodes 106 can be selected to increase the likelihood that the current passing through any one of the return electrodes 106 is likely to remain below a predetermined threshold (e.g., to reduce the likelihood of damage to skin of the patient) during the treatment.

In general, the return electrodes 106 can be substantially similar to one another. However, unless the distribution of the electrical energy through return electrodes 106 is controlled, differences in the distribution of the electrical energy moving from the ablation electrode 112 through the return electrodes 106 can exist during the medical treatment. Such differences can be attributable, for example, to one or more of normal manufacturing differences between the return electrodes 106, differences in contact area between each one of the return electrodes 106 and skin of the patient 102, and differences in position of the return electrodes 106 relative to the ablation electrode 112. While manual adjustments (e.g., repositioning the return electrodes 106) can be made to address these differences to a degree, such manual adjustments can be time-consuming and disruptive from a workflow perspective, given that power is delivered after the patient has been positioned and the catheter 104 has been inserted and delivered to the treatment site. Additionally, or alternatively, such manual adjustments can continue to be required as conditions change during the medical treatment.

The controller 108 can include circuitry to control distribution of the electrical energy among the return electrodes 106 with the return electrodes 106 in a fixed position in contact with skin of the patient. That is, the controller 108 can distribute electrical energy from the ablation electrode 112 to the return electrodes 106 without requiring manipulation of the return electrodes 106. As used herein, it should be understood that the distribution of electrical energy can include distribution of current, voltage and energy, unless otherwise specified or made clear from the context.

In general, the distribution of the electrical energy by the controller 108 can be any one or more distributions suitable for a particular application. For example, the controller 108 can maintain at least one of an electrode current and an electrode voltage in each of the return electrodes 106 below a predetermined threshold (e.g., below about 1 ampere to reduce the likelihood of damage to tissue). Additionally, or alternatively, the distribution of the electrical energy by the controller 108 can be a substantially uniform distribution of at least one of current and voltage among the return electrodes 106 such that a respective one of the electrode current and the electrode voltage in the return electrodes 106 is substantially equal.

Figure 2:
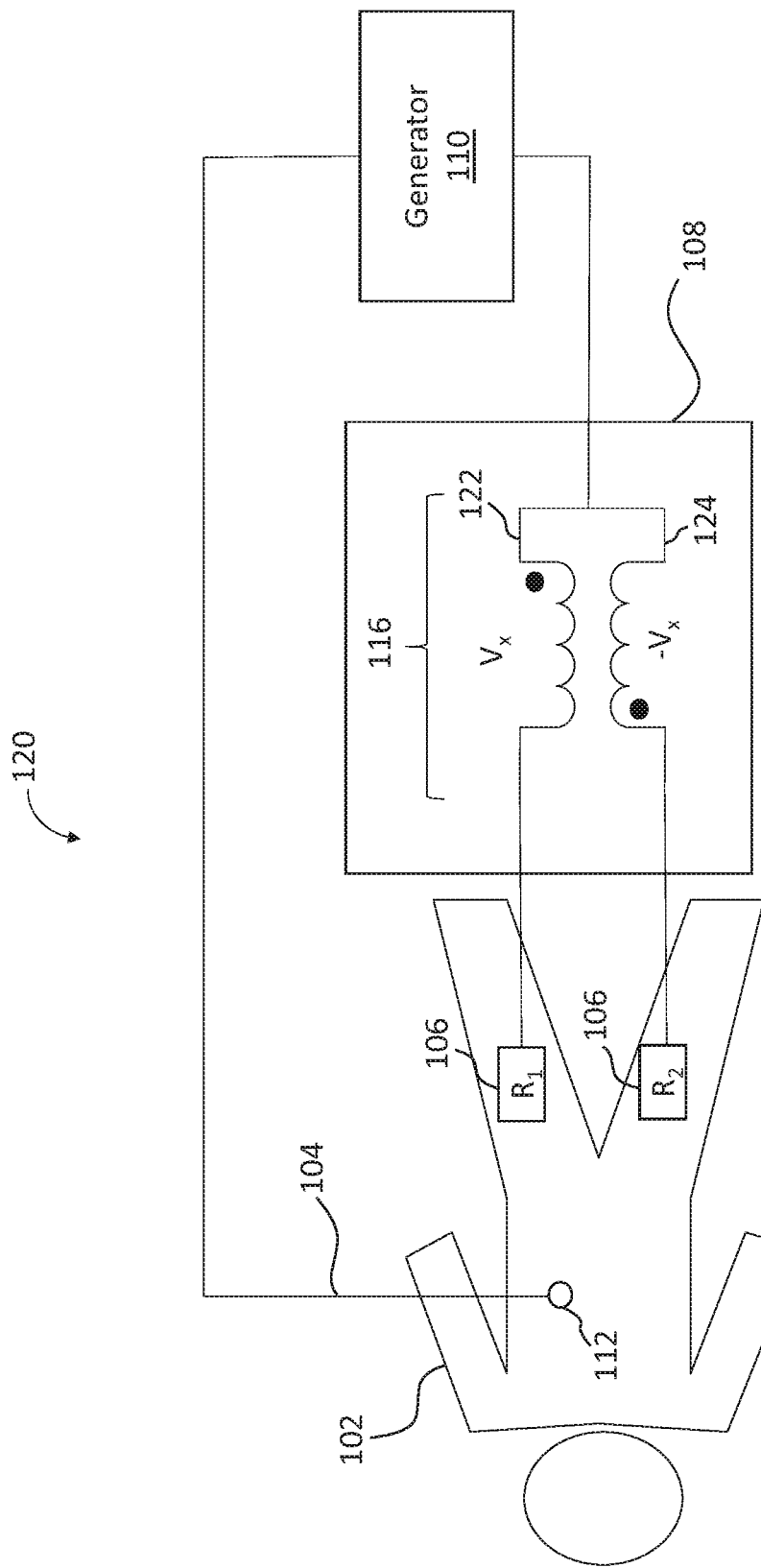
FIG. 2 is an electric circuit diagram of the tissue ablation system of FIG. 1, with the controller including a transformer.

Referring now to FIGS. 1 and 2, the controller 108 can include a transformer 116 in electrical communication with each combination of at least two of the return electrodes 106. It should be understood that because the return electrodes 106 are shown as including a single pair, the transformer 116 is shown as a single transformer in FIG. 2. As described in greater detail below, additional transformers can be used in implementations in which the system includes more than two return electrodes.

Referring now to FIG. 2, an electric circuit 120 represents the flow of electrical energy through the tissue ablation system 100 (FIG. 1) during a medical treatment performed on the patient 102 (FIG. 1). The transformer 116 can include a primary winding 122 and a secondary winding 124. The transformer 116 can be modeled, for example, as an ideal transformer. The primary winding 122 can be in series with a first impedance $R_1$, and the secondary winding 124 can be in series with a second impedance $R_2$. The first impedance $R_1$ is the impedance associated with one of the return electrodes 106 (FIG. 1) on skin of the patient 102, and the second impedance $R_2$ is the impedance associated with the other one of the return electrodes 106 (FIG. 1) on skin of the patient 102.

As electrical energy is driven by the generator 110, a voltage V develops across the generator 110. If there is an impedance mismatch between the return electrodes 106, the primary winding 122 will have a voltage $V_x$ and the secondary winding 124 will have a voltage $-V_x$. Accordingly, the voltage across one of the return electrodes 106 will be $V+V_x$ while the voltage across the other one of the return electrodes 106 will be $V-V_x$ such that the current through each of the return electrodes 106 is the same. That is, if there is an impedance mismatch between the first impedance $R_1$ and the second impedance $R_2$, the transformer 116 balances the current passing through the first impedance $R_1$ and the second impedance $R_2$ such that the current passing through the return electrodes 106 is equal. It should be appreciated that, in the degenerate case in which the first impedance $R_1$ is equal to the second impedance $R_2$, the voltage $V_x$ is zero.

Figure 3:
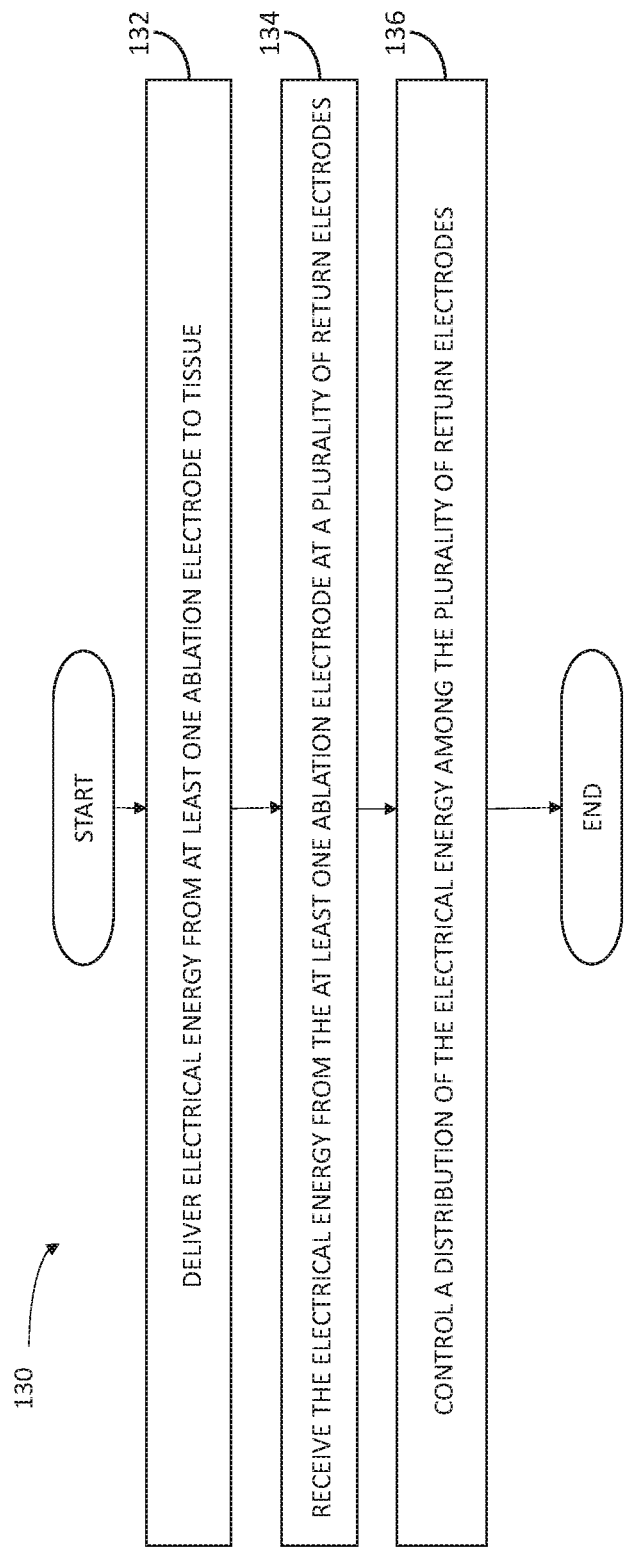
FIG. 3 is a flowchart of a method of ablating tissue.

FIG. 3 is a flowchart of a method 130 of ablating tissue. Unless otherwise specified or made obvious from the context, the method 130 can be carried out using any one or more of the systems and devices described herein. At block 132, the method 130 can include delivering electrical energy from at least one ablation electrode to tissue at a treatment site within an anatomic structure of a patient. Continuing at block 134, the method 130 includes receiving the electrical energy from the at least one ablation electrode at a plurality of return electrodes. The method 130 continues at block 136 with controlling a distribution of the electrical energy among the plurality of return electrodes. The return electrodes can be external to the patient and in contact with the skin of the patient, and the distribution of the electrical energy can be controlled (block 136) with the return electrodes in a fixed position in contact with skin of the patient. Thus, for example, the method 130 can facilitate achieving a desired distribution of the electrical energy without requiring repositioning of the return electrodes.

Delivering electrical energy from the at least one ablation electrode to tissue at the treatment site within the anatomic structure of the patient (block 132) can include driving the electrical energy from the ablation electrode to the tissue through one or more of the generators described herein (e.g., the generator 110 in FIGS. 1 and 2). For example, delivering the electrical energy from the at least one ablation electrode can include ablating tissue in a cardiac chamber of the patient. Continuing with this example, delivering the electrical energy from the at least one ablation electrode can include forming one or more lesions in the tissue as part of a treatment of cardiac arrhythmias.

Receiving the electrical energy from the at least one ablation electrode at the plurality of return electrodes (block 134) can include passing the electrical energy from tissue in an anatomic structure of the patient to the return electrodes positioned on skin of the patient. In certain implementations, the electrical energy can be received at the return electrodes at the same time. Further, or instead, as described in greater detail below, the electrical energy can be received at the return electrodes individually (e.g., through time-division multiplexing).

In general, controlling the distribution of the electrical energy among the plurality of return electrodes (block 136) can include controlling distribution of one or more of current and voltage among the return electrodes. It should be appreciated that controlling the distribution of the electrical energy among the plurality of return electrodes can include directing the electrical energy through any one or more of the controllers described herein. Thus, for example, controlling the distribution of the electrical energy can include directing the electrical energy through one or more transformers (e.g., through the controller 108 shown in FIGS. 1 and 2) in electrical communication with at least two of the return electrodes.

In certain implementations, controlling the distribution of the electrical energy among the plurality of return electrodes (block 136) can include substantially uniformly distributing at least one of current and voltage of the electrical energy among the plurality of return electrodes. Such a substantially uniform distribution can be useful, for example, for making the most efficient use of the return electrodes. That is, the substantially uniform distribution of at least one of current and voltage can facilitate controlling the electrical energy using fewer return electrodes since it reduces the likelihood of excessive current in any one of them.

In some implementations, controlling the distribution of the electrical energy among the plurality of return electrodes (block 136) can include maintaining an electrode current or an electrode voltage in each respective return electrode below a predetermined threshold. For example, in instances in which an electrode current in each respective return electrode is maintained below a predetermined threshold, the predetermined threshold can be less than about 1 ampere (e.g., about 0.7 amperes). More generally, the predetermined threshold can be associated with reducing the likelihood of a concentration of energy that would cause an unintended change in tissue away from the treatment site.

Although the steps of the method 130 are discussed and/or illustrated in a particular order, the method 130 shown in FIG. 3 is not so limited. In other implementations, the method 130 can be performed in a different order. In these and other implementations, any of the steps of the method 130 can be performed before, during, and/or after any of the other steps of the method 130. Moreover, a person of ordinary skill in the relevant art will readily recognize that the illustrated method 130 can be altered and still remain within these and other implementations of the present technology. For example, one or more steps of the method 130 illustrated in FIG. 3 can be omitted and/or repeated in some implementations.

Figure 4:
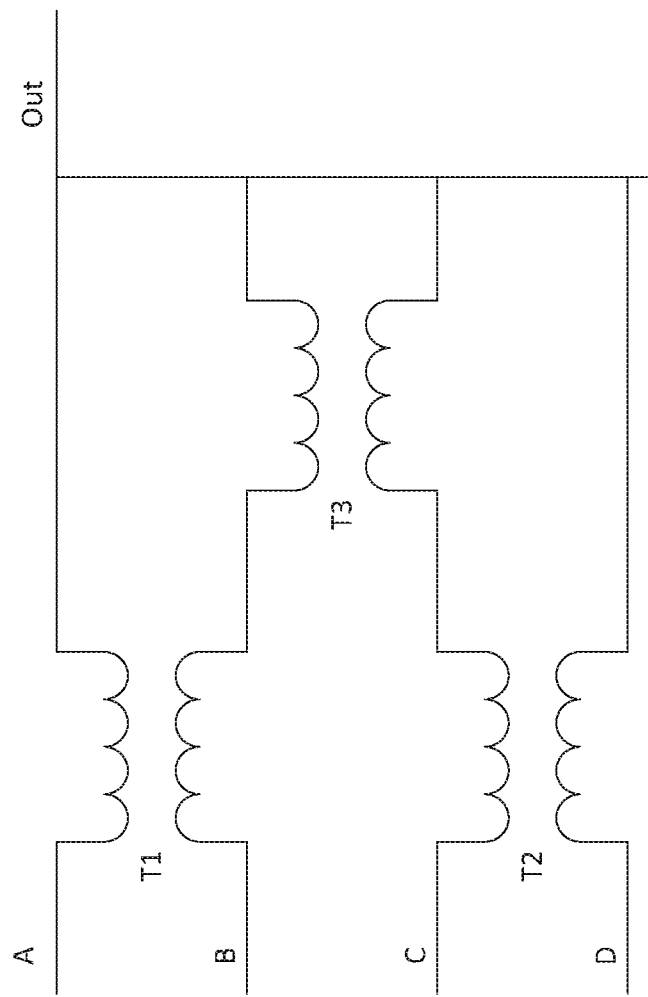
FIG. 4 is a schematic representation of a portion of electrical circuit of an implementation in which energy moving between an ablation electrode and four return electrodes is balanced through an arrangement of three transformers.
Figure 5:
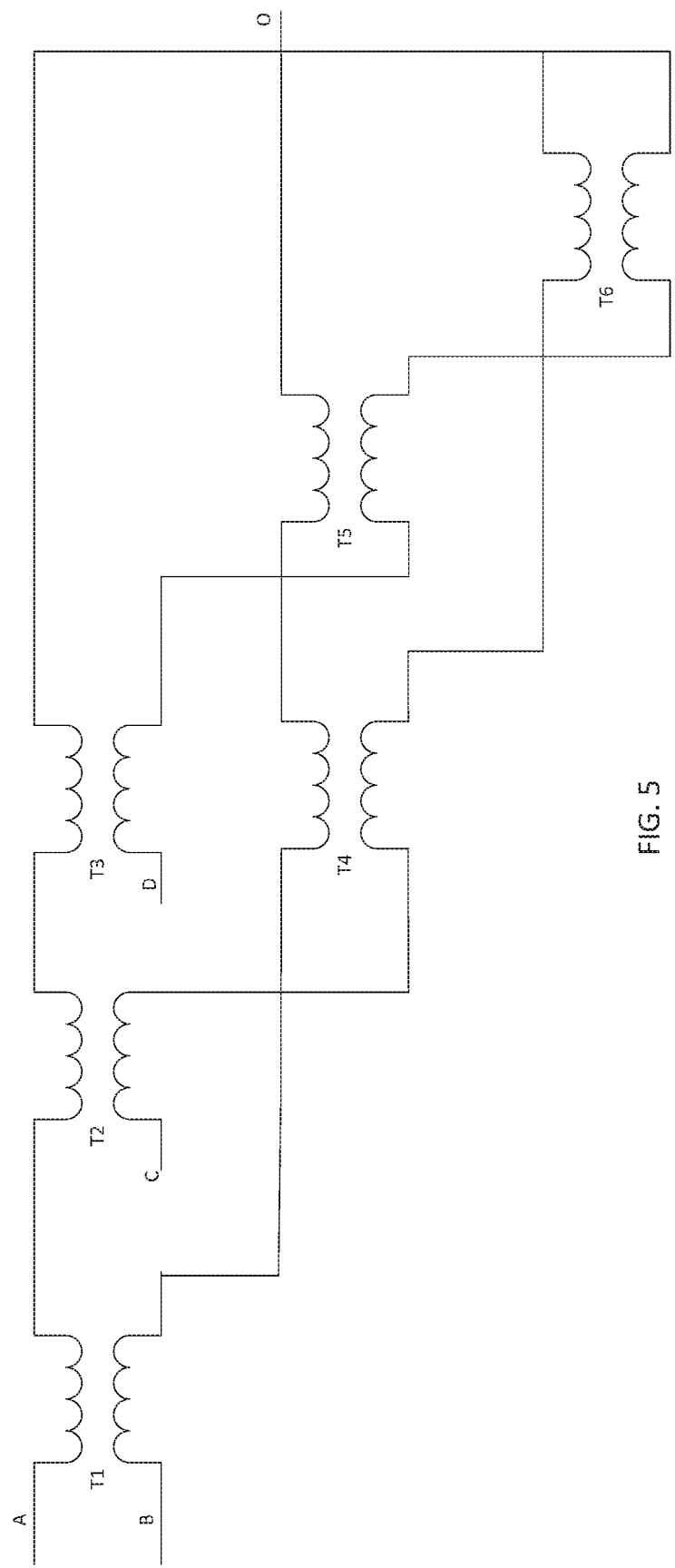
FIG. 5 is a schematic representation of a portion of an electric circuit in which energy from an ablation electrode can be distributed among four return electrodes.
Figure 6:
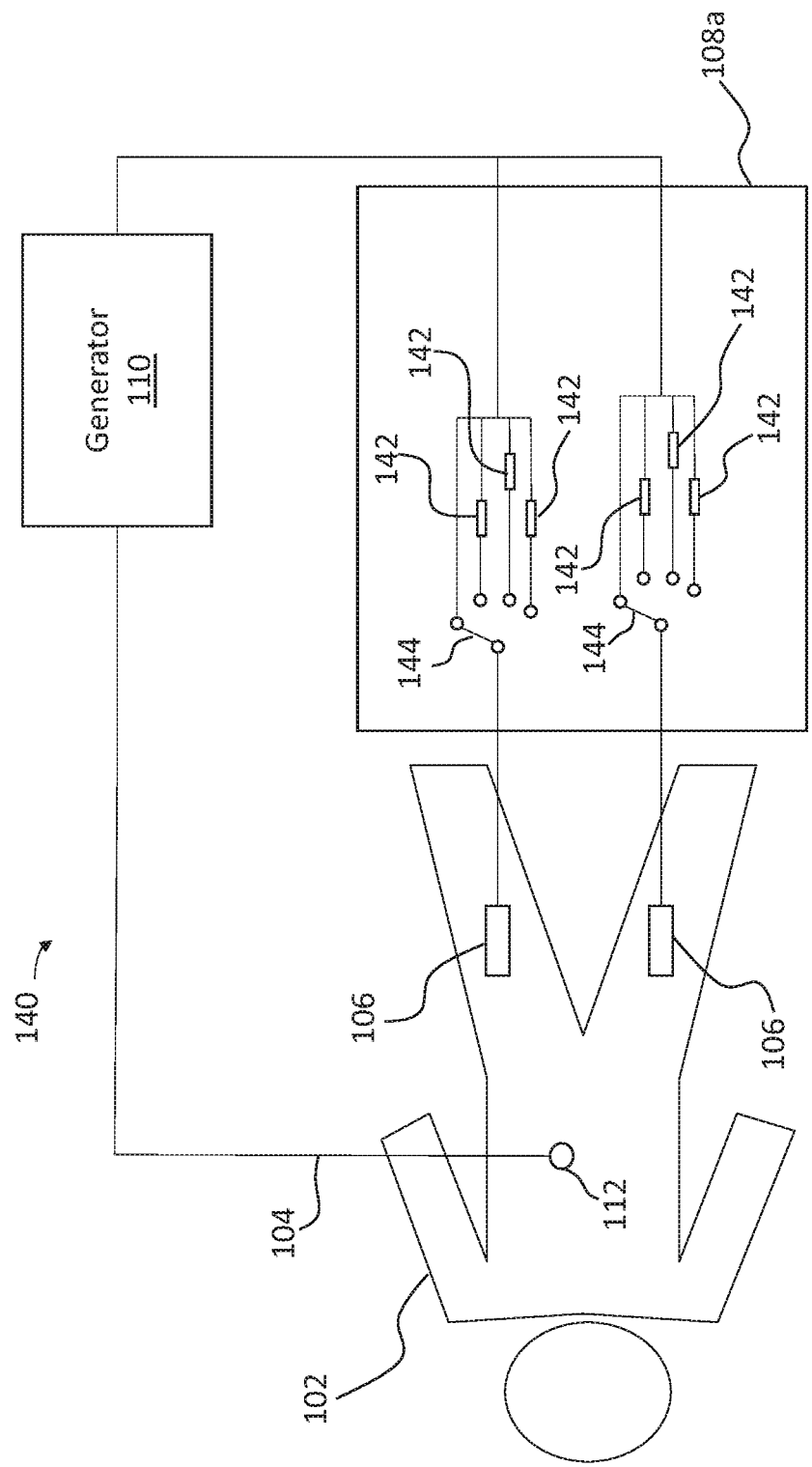
FIG. 6 is an electric circuit diagram of the tissue ablation system of FIG. 1, with the controller including resistors and a switch.
Figure 7:
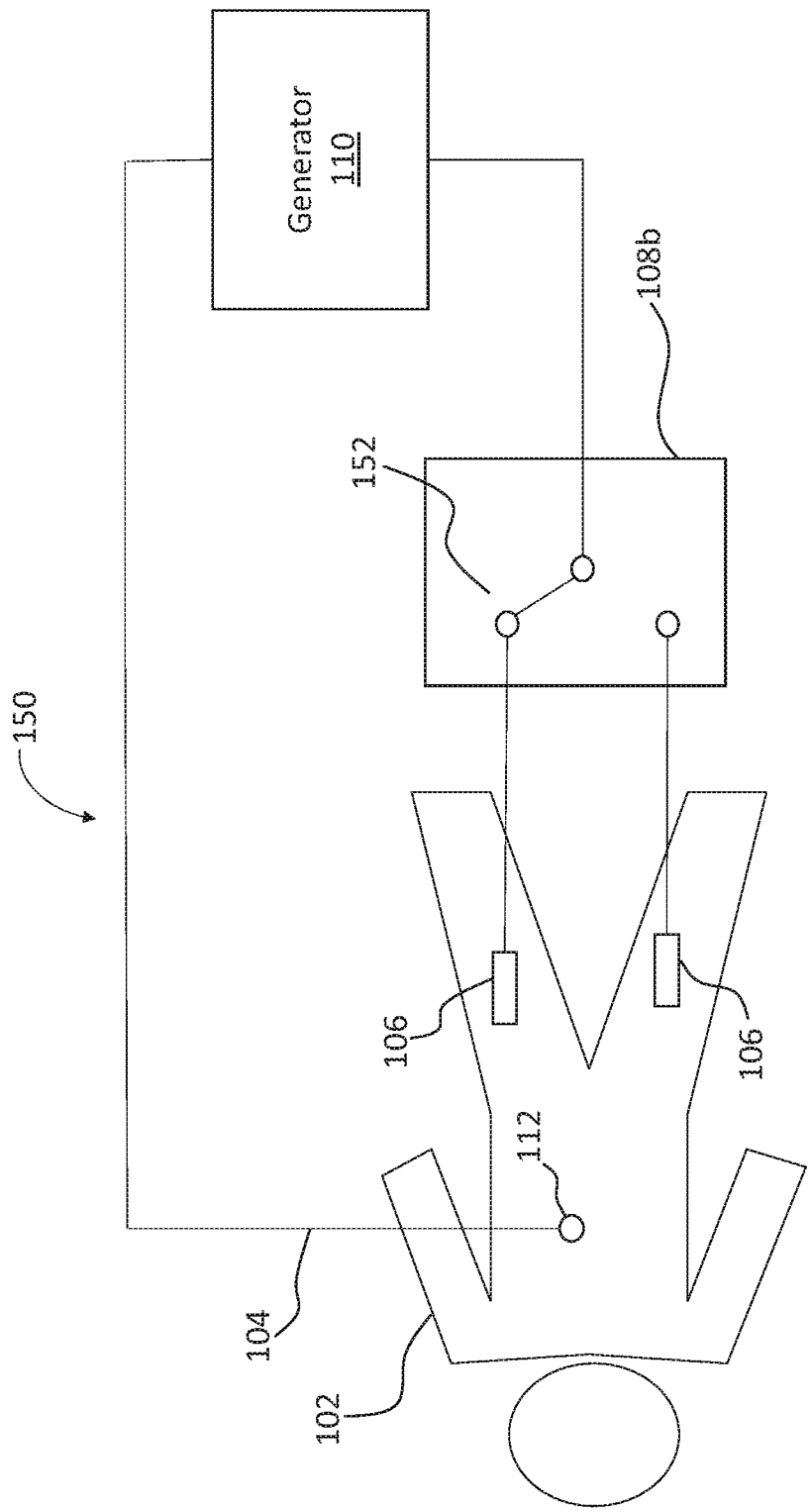
FIG. 7 is an electric circuit diagram of the tissue ablation system of FIG. 1, with a controller including a multiplexer.

While certain implementations have been described, other implementations are additionally or alternatively possible. As an example, while the controller has been described as including two return electrodes, it should be appreciated that controllers can additionally, or alternatively, include more than two return electrodes. In general, energy passing through more than two return electrodes can be balanced through the use of one or more transformers. Examples of transformer arrangements useful for balancing energy among more than two return electrodes are shown in FIGS. 4 and 5. Unless otherwise indicated or made clear from the context, the return electrodes A, B, C, D should be understood to be identical to the return electrodes 106 (FIGS. 1 and 2), and the transformers T1, T2, T3, T4, T5, and T6 should be understood to be identical to the transformer 116 (FIG. 2).

FIG. 4 is a schematic representation of a portion of an electrical circuit of an implementation in which energy moving between an ablation electrode (e.g., ablation electrode 112 in FIG. 1) and four return electrodes A, B, C, D can be balanced through an arrangement of three transformers T1, T2, T3. In such instances, a first electrode pair A-B can be balanced through the transformer T1, and a second electrode pair C-D can be balanced through the transformer T2. The electrode pairs A-B and C-D can be balanced through the transformer T3 so that all four return electrodes A, B, C, D receive the same current.

Additionally, the controller can include one transformer for each combination of pairs of electrodes in a plurality of return electrodes. FIG. 5 is a schematic of a portion of an electric circuit in which energy from an ablation electrode (e.g., ablation electrode 112 in FIG. 1) can move among four return electrodes A, B, C, D, with each pair of electrodes (A-B, A-C, A-D, B-C, B-D, and C-D) balanced through electrical communication with transformers T1-T6. As compared to the configuration of transformers in FIG. 4, it should be appreciated that the configuration of transformers in FIG. 5 can have a lower residual voltage across each transformer. Additionally, it should be understood that, in FIG. 5, each pair of electrodes is shown separately, rather than depicting multiple connections extending from each return electrode A-D to the transformers T1-T6.

As another example, while a controller has been described as including one or more transformers, it should be appreciated that controllers can additionally, or alternatively, include other electrical components for controlling distribution of electrical energy to a plurality of return electrodes. For example, referring now to FIGS. 1 and 6 together, electric circuit 140 represents the flow of electrical energy through the tissue ablation system 100, with a controller 108a including resistors 142 and switches 144 in electrical communication with one another to control one or more of current and voltage applied to the respective return electrodes 106. Unless otherwise specified or made clear from the context, the controller 108a should be understood to be interchangeable with or used in addition to the controller 108 described with respect to FIG. 2. Further, or instead, unless otherwise specified or made clear from the context, the controller 108a should be understood to be operable as part of the tissue ablation system 100 carrying out any one or more of the methods described herein, including the method 130 described with respect to FIG. 3.

In use, each switch 144 can be actuatable to change a path of electrical energy in the tissue ablation system 100 to change the resistance associated with a respective one of the return electrodes 106. For example, the resistors 142 can be arranged such that activation of one or more of the switches 144 can connect one or more of the resistors 142 in series with the respective return electrode 106. It should be appreciated that the electrode current in the respective return electrode 106 can decrease as the switch 144 is activated. Additionally, or alternatively, deactivation of one or more of the switches 144 can disconnect one or more of the resistors 142 from connection to the respective return electrode 106. The electrode current in one or more of the return electrodes 106 can increase as the switch 144 is deactivated.

The activation of one or more of the switches 144 can be based on an upper threshold of current detected in one or both of the return electrodes 106. Also, or instead, the deactivation of one or more of the switches 144 can be based on a lower threshold of current detected in one or both of the return electrodes 106.

As another example, while electrical energy has been described as being applied to return electrodes simultaneously, it should be appreciated that the electrical energy can be time-divided between at least one ablation electrode and a plurality of return electrodes. For example, referring now to FIGS. 1 and 7 together, an electric circuit 150 represents the flow of electrical energy through the tissue ablation system 100, with a controller 108b including a multiplexer 152 to control one or more of current and voltage through the return electrodes 106. Unless otherwise specified or made clear from the context, the controller 108b should be understood to be interchangeable with or used in addition to one or more of the controllers 108 described with respect to FIG. 2 and the controller 108a described with respect to FIG. 6. Further, or instead, unless otherwise specified or made clear from the context, the controller 108b should be understood to be operable as part of the tissue ablation system 100 carrying out any one or more of the various different methods described herein, including the method 130 described with respect to FIG. 3.

Each return electrode 106 can be in electrical communication with the generator 110 through a respective channel of the multiplexer 152. In use, the multiplexer 152 can switch between the channels (e.g., cycling sequentially among the channels) such that each of the return electrodes 106 can be in electrical communication with the generator 110, independently of the electrical communication between the generator 110 and each of the other return electrodes 106. Thus, for example, by rapidly cycling the multiplexer 152 between the return electrodes 106 to make and break electrical communication between the generator 110 and each of the return electrodes 106, one or more of the electrode current and electrode voltage of each of the return electrodes 106 can be controlled independently of the electrical energy delivered to the other return electrodes 106.

In certain implementations, the multiplexer 152 can include a make-before-break switch. During switching between the return electrodes 106, the make-before-break switch can maintain a connection with a first one of the return electrodes 106 until a connection with a second one of the return electrodes 106 is made. As compared to switching before a connection to another one of the return electrodes 106 is made, make-before-break switching can be useful for reducing load fluctuations experienced by the generator 110.

As still another example, while electrical energy has been described as being applied to return electrodes using a single generator, it should be appreciated that the electrical energy can be delivered to each of the return electrodes through a respective generator. For example, referring to FIG. 1, the generator 110 can include a plurality of generators such that each generator is in electrical communication with a respective one of the return electrodes 106 and the ablation electrode 112. In such implementations, the plurality of generators can be electrically isolated from one another. Additionally, or alternatively, the plurality of generators can be electrically isolated from one another over a predetermined frequency range (e.g., a frequency range of the electrical energy directed from the ablation electrode 112 to the tissue during treatment). In certain instances, the controller 108 can control each generator to drive electrical energy between the ablation electrode 112 and the respective one of the return electrodes 106.

As another example, while driving a balanced distribution of electrical energy from an ablation electrode to one or more return electrodes has been described, electrical energy can be driven from an ablation electrode to one or more return electrodes based on additional or alternative considerations. For example, in certain applications, reducing the likelihood of unintended tissue damage associated with electrical energy driven through the one or more return electrodes can be a multi-faceted control challenge—specifically, one with both instantaneous and cumulative aspects, each of which must be addressed and each of which can become increasingly relevant as larger amounts of power are delivered through an ablation electrode. Thus, while balancing a distribution of electrical energy can be useful for addressing certain instantaneous aspects associated with unintended tissue damage, energy delivered to the ablation electrode can additionally or alternatively be selectively controlled to account for cumulative effects of electrical energy passing through the one or more return electrodes. Further, or instead, as described in greater detail below, a combination of balanced distribution of electrical energy and selective control can be useful for predicting (e.g., before electrical energy is delivered) whether a lesion can be formed safely and, thus, can reduce the need to interrupt lesion formation.

Figure 8:
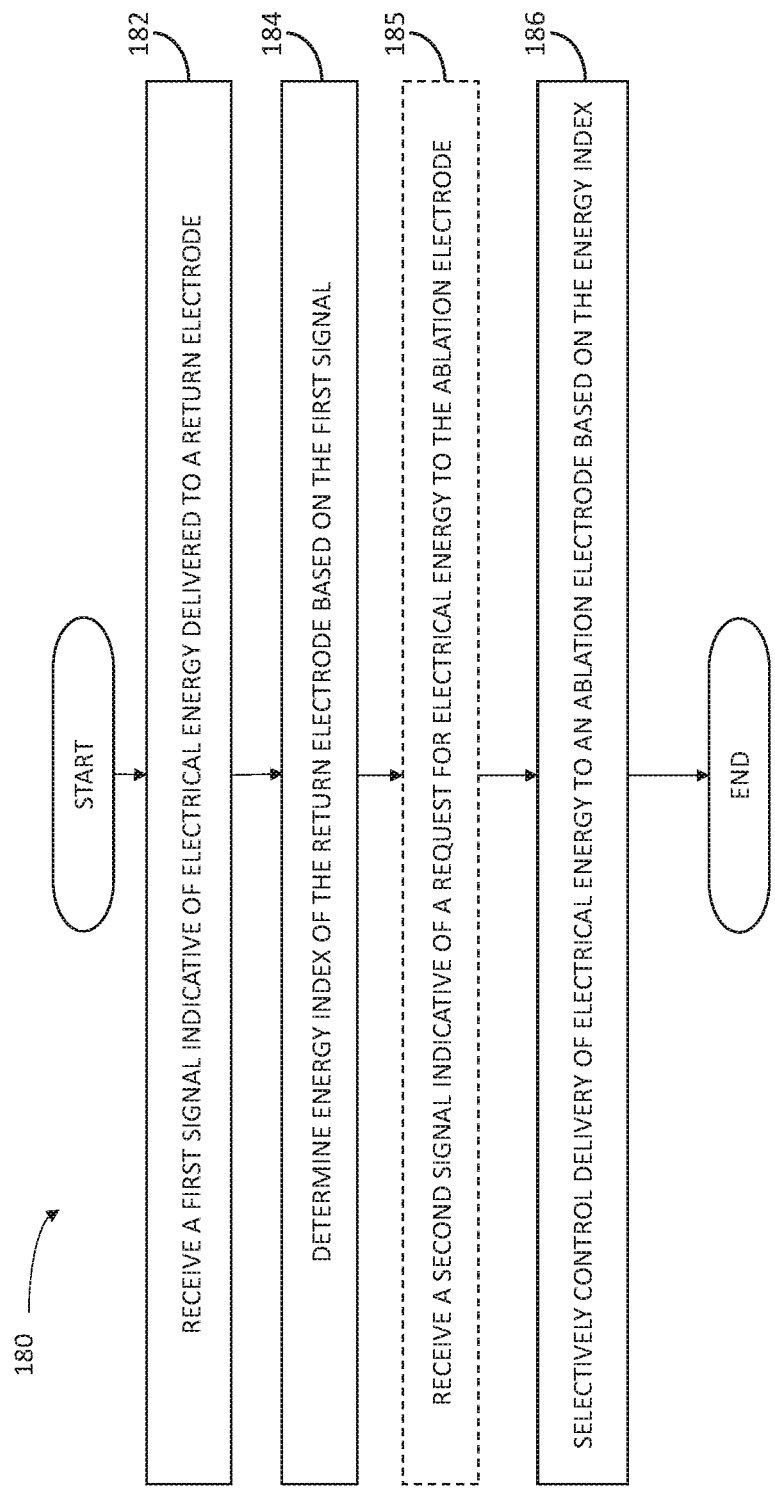
FIG. 8 is a flowchart of a method of selectively controlling delivery of electrical energy to an ablation electrode.

FIG. 8 is a flowchart of a method 180 of controlling lesion formation by an ablation electrode disposed in an anatomic structure of a patient. Unless otherwise specified or made obvious from the context, the method 180 can be carried out using any one or more of the systems and devices described herein and can be carried out in combination with any one or more of the methods described herein. Thus, for example, the controller 108 (FIG. 1) can include a non-transitory, computer-readable storage medium having stored thereon computer-executable instructions for causing one or more processors to carry out the method 180, which can include receiving a first signal indicative of electrical energy delivered to a return electrode in electrical communication with the ablation electrode (block 182), determining an energy index of the return electrode and, based on the energy index associated with the return electrode (block 184), and selectively controlling delivery of electrical energy to the ablation electrode (block 186).

At block 182, receiving the first signal indicative of the electrical energy delivered to the return electrode can include receiving an indication of one or more of current, impedance, voltage, or power associated with the return electrode. In general, the first signal can be measured according to any one or more methods well-known in the art, such as measuring voltage drop across an in-line resistor, the use of a Hall-effect sensor, a transformer, etc. The first signal can be continuous or substantially continuous to facilitate, among other things, real-time control. Further, or instead, the first signal can be substantially isolated from other return electrodes in instances in which multiple return electrodes are used as return paths for electrical energy driven by the ablation electrode into the treatment site.

The received first signal (block 182) shall be understood to include any signal or signal-derived parameter useful for determining the energy index (block 184) according to any one or more of the techniques described herein. Thus, unless otherwise specified or made clear from the context, the received first signal shall be understood to be based on any one or more of various, different types of measured raw signals and, optionally, can be based on any manner and form of signal processing applied to the measured raw signal. For example, the received first signal can be based on a substantially constant measured raw signal over at least a portion of a period of a medical treatment. More typically, however, the received first signal can be based on a measured raw signal that temporally varies (e.g., a sinusoidal signal or another type of signal having a regular temporal variation, such as certain types of step functions) over at least a portion of a period of a medical treatment. In certain implementations, the received first signal can be based on one or more computations applied to the measured raw signal and/or applied to a signal derived from the measured raw signal. Thus, for example, the received first signal can be based on the root-mean-square of the measured raw signal and/or a signal based on the measured raw signal, with the use of the root-mean-square being particularly usefully applied to derivation of the received first signal from a measured raw signal characterized by sinusoidal variation. As an additional or alternative example, the received first signal can be based on the amplitude or other temporal computation (e.g., mean of an absolute value) applied to the measured raw signal and/or to a signal based on the measured raw signal.

In general, determining the energy index (block 184) can be based on the first signal received (block 182) in a current time-step and the first signal received in one or more time-steps preceding the current time-step. That is, the energy index can be a parameter directly or indirectly indicative of cumulative energy passing through the return electrode. Accordingly, the energy index can serve as a useful proxy for a likelihood of unintended tissue damage in the vicinity of the return electrode, and selectively controlling delivery of electrical energy to the ablation electrode based on such an energy index (block 186) can be useful for reducing the likelihood of unintended tissue damage associated with cumulative exposure to electrical energy.

In certain implementations, determining the energy index of the return electrode (block 184) can be based on the first signal received (block 182) over a temporal window having a predetermined duration. As an example, the first signal received over the temporal window can be derived from a measured raw signal processed through a finite impulse response (FIR) filter. The predetermined duration can be a fixed duration in some instances (e.g., based on guidelines or observations regarding unintended tissue damage through cumulative exposure to electrical energy). Additionally, or alternatively, the predetermined duration can be adjustable by a physician through a user input device.

In some implementations, determining the energy index of the return electrode (block 184) can be based on the first signal received (block 182) over an infinite temporal window. As an example, the received first signal can be derived from a measured raw signal processed through an infinite impose response (IIR) filter.

The energy index can be based on any manner and form of summing the first signal over the temporal window. In general, the energy index can be based on a linear or nonlinear function of the first signal. Thus, in instances in which the first signal is indicative of current through the return electrode, the energy index can be based on a weighted sum of a nonlinear function of the indication of the current through the return electrode over the temporal window. As a more specific example, the weighted sum of the indication of current can include weighting recent time-steps more heavily than older time-steps which, as compared to an equal weighting of the indication of current over all time-steps, can be a more accurate predictor of unintended tissue damage. Additionally, or alternatively, the energy index can be based on a heating factor which, as used herein, shall generally be understood to be current raised to a power greater than one (e.g., a power of 2) and summed—with or without weighting—over a predetermined temporal window. For example, the heating factor can be a heating factor as described in the International Electrotechnical Commission (IEC) 60601-2-2:2017 standard entitled "Medical electrical equipment—Part 2-2: Particular requirements for the basic safety and essential performance of high frequency surgical equipment and high frequency surgical accessories" (hereinafter, *IEC 60601-2-2:2017*), the entire contents of which are incorporated herein by reference.

Selectively controlling delivery of electrical energy to the ablation electrode (block 186) can include selectively interrupting energy delivery to the ablation electrode and/or selectively enabling energy delivery to the ablation electrode based on the energy index. Examples of selectively interrupting energy delivery and selectively enabling energy delivery to the ablation electrode are provided in the description that follows. In general, however, selectively controlling delivery of electrical energy (block 186) can include comparing the energy index to a predetermined threshold or, in some cases, to a plurality of thresholds. The predetermined threshold can be, for example, a fixed parameter, such as a parameter based on an industry standard. As a more specific example, the predetermined threshold can be a heating factor of 30 amperes$^2$ over 60 seconds, as specified in *IEC 60601-2-2:2017*. Further, or instead, the predetermined threshold can be a variable set by the physician as an input through a user input device (such as through the catheter interface unit 114 in FIG. 1). For example, through the user input device, the physician can set the predetermined threshold to a value suitable to account for one or more clinical considerations and/or to increase a margin of safety.

In certain implementations, selectively controlling delivery of electrical energy to the ablation electrode (block 186) can include feedback control based on comparing the energy index of the return electrode, at each time-step, to a predetermined threshold. As used herein, the term "feedback control" should be understood to include any manner and form of controlling delivery of electrical energy to the ablation electrode based at least in part on the energy index in a present time-step or in one or more previous time-steps. Further, while selectively controlling delivery of electrical energy to the ablation electrode (block 186) is described in terms of feedback control and predictive control approaches below, it should be appreciated that the distinction herein between feedback control and predictive control is for the sake of clarity and efficiency of explanation. Thus, unless otherwise specified or made clear from the context, any one or more control approaches described herein can be combined to selectively control delivery of electrical energy to the ablation electrode.

As an example of a feedback control implementation, the energy index of the return electrode can be compared to the predetermined threshold at each time-step and, once the energy index associated with a given time-step is at or above the predetermined threshold, the energy delivery to the ablation electrode can be interrupted. Such feedback control can be useful for providing robust and reliable protection against unintended tissue damage. For example, feedback control of this type can be particularly useful for use with a system including a plurality of return electrodes arranged such that the electrical energy through each return electrode can be dissimilar, which is characteristic of conventional systems. More specifically, in a system including an ablation electrode driving electrical energy to a plurality of return electrodes, feedback control of this type can be implemented at each return electrode, and the electrical energy to the ablation electrode can be interrupted if the respective energy index of any one of the return electrodes exceeds a predetermined threshold.

While selectively interrupting electrical energy to the ablation electrode can be useful for protecting against unintended tissue damage at the return electrodes, such interruption of electrical energy can result in a corresponding interruption in lesion formation. As is generally understood, interrupting lesion formation can complicate completion of the ablation treatment—edema in partially ablated tissue can make the partially ablated tissue difficult to discern from fully ablated tissue and can make the tissue more difficult to ablate using RF energy. Thus, in certain implementations, feedback control can include disabling delivery of electrical energy to the ablation electrode. For example, in implementations in which the predetermined threshold is 30 amperes$^2$ per 60 seconds, and the energy index is at 29 amperes$^2$ per 60 seconds at a present time-step following formation of a lesion, immediately delivering additional electrical energy to form the subsequent lesion may have a high likelihood of resulting in interruption of the subsequent lesion. Thus, continuing with this example, delivery of electrical energy to the ablation electrode can be disabled until the energy index of a present time-step is below 15 amperes$^2$ per 60 seconds or some other suitable value. Disabling delivery of electrical energy in this way can increase the likelihood that the subsequent lesion can be formed without interruption. In general, it should be appreciated that these values are presented for the sake of an illustrative example of the concept, and other values can further or instead be useful for a given implementation.

In some implementations, selectively controlling delivery of electrical energy to the ablation electrode (block 186) can advantageously include selectively enabling energy delivery to the ablation electrode based on predictive control to reduce the likelihood of needing to interrupt lesion formation. As used herein, the term "predictive control" should be understood to include any manner and form of control based on an amount and duration of electrical energy to the ablation electrode that has been requested (e.g., through actuation of a user input device) but not yet delivered to the ablation electrode.

In certain instances, the method 180 can further, or instead, include receiving a second signal indicative of a request for electrical energy to the ablation electrode (block 185). The request for electrical energy to the ablation electrode can be input by a physician through any one or more user input devices operated or controlled by the physician during a medical procedure. Thus, for example, the request for electrical energy can be a variable input provided by the physician. Further or instead, the request for electrical energy can be substantially constant. The request for electrical energy to the ablation electrode can include, for example, a maximum current and a duration of electrical energy to be delivered to the ablation electrode to form the next lesion at the treatment site. In general, the maximum current of electrical energy to be delivered to the ablation electrode can correspond to a value resulting in a safe amount of current passing through each return electrode. More specifically, the maximum current of electrical energy to be delivered to the ablation electrode can correspond to a current greater than zero and less than about 1 ampere in each return electrode.

In the context of predictive control, selectively controlling delivery of electrical energy to the ablation electrode (block 186) can include enabling delivery of the requested electrical energy based on whether the energy index of a present time-step and/or one or more previous time-steps is below a predetermined threshold. Further, or instead, a projected increase in the energy index of the return electrode in one or more future time-steps can be determined and form a basis for whether the requested electrical energy can be safely delivered to the ablation electrode. Continuing with this example, if the energy index of the return electrode and the projected increase of the energy index of the return electrode in some combination is below a predetermined threshold, the delivery of the requested electrical energy to the ablation electrode can be enabled. As an example, the energy index and the projected increase of the energy index can be combined in an unweighted sum and compared to a predetermined threshold to determine whether to enable delivery of the requested electrical energy to the ablation electrode. More generally, any one or more of various different combinations of the energy index and the projected increase of the energy index can be useful for forming a basis for determining whether to deliver the requested electrical energy. For example, while an unweighted sum has been described and can be useful in certain instances, it should be appreciated that any one or more types of combinations are additionally, or alternatively, possible. For example, weighted sums can be further or alternatively useful as a basis for selectively controlling delivery of electrical energy to the ablation electrode. Continuing with this example, the energy index of the return electrode and the projected increase of the energy index of the electrode can be combined according to a weighted sum in which the weights depend on the duration of the requested energy delivery. As another example, while the energy index and the projected increase of the energy index have been described as being a sum, it should be appreciated that nonlinear combinations are additionally or alternatively possible.

In many implementations, electrical energy delivered to the ablation electrode can return through a plurality of return electrodes. Thus, in such implementations, receiving the first signal indicative of electrical energy in the return electrode (block 182) can include selecting the first signal from a plurality of signals. Each signal of the plurality of signals can be indicative of current (or another electrical parameter) in a respective return electrode of the plurality of return electrodes.

In general, the method 180 can be carried out for each return electrode of the plurality of return electrodes. In the case of feedback control, extension of the method 180 to a system including a plurality of return electrodes can be straightforward. In the case of predictive control, however, a system including a plurality of return electrodes presents complexity that is not present in the case of a system including a single return electrode or in the case of feedback control. That is, to carry out predictive control effectively in a system including a plurality of return electrodes, there exists a need to account for how the requested electrical energy will be distributed among the plurality of return electrodes such that, in turn, a useful determination of a respective energy index associated with each return electrode can be made.

In certain implementations of predictive control, selectively controlling delivery of the electrical energy to the ablation electrode (block 186) can be based on an estimate of a distribution of the requested electrical energy among the plurality of return electrodes. As an example, an estimate of the distribution of the requested electrical energy can be based on a distribution of electrical energy associated with at least one time-step preceding the current time-step. Such an estimate can be useful, for example, for at least partially accounting for temporal variations in the distribution of electrical energy through the plurality of return electrodes. As an additional or alternative example, an estimate of the distribution of the requested electrical energy can be based on an equal distribution of electrical energy (e.g., current and/or voltage) associated with at least one time-step preceding the current time-step. Such an equal distribution of electrical energy can be a particularly appropriate representation of the flow of electrical energy imposed by certain hardware configurations, such as any one or more of the devices and systems described with respect to FIGS. 1-7. Stated differently, by providing an equal distribution of electrical energy flowing through the return electrodes, the devices and systems described with respect to FIGS. 1-7 can be particularly well-suited for use in carrying out the method 180 in instances in which selectively controlling delivery of electrical energy to the ablation electrode (block 186) is based on one or more forms of predictive control.

While selectively controlling delivery of electrical energy to the ablation electrode (block 186) has been described as selectively interrupting and/or enabling delivery of energy to the ablation electrode, other hardware components (e.g., a button, a foot pedal, a touch screen, etc.) can be selectively changed in coordination with the selective interruption and/or enabling of energy delivery to the ablation electrode.

As an example, a user interface associated with the ablation electrode can be selectively enabled/disabled or otherwise modified as part of selectively controlling delivery of electrical energy to the ablation electrode (block 186), with the modification providing the physician with useful feedback regarding whether energy is currently deliverable to the treatment site through the ablation electrode. Thus, in instances in which the user interface includes a foot pedal, the process at block 186 of selectively controlling delivery of electrical energy to the ablation electrode can include locking or unlocking movement of the foot pedal according to a state of the selective control. During the course of the procedure, whether or not the foot pedal is movable can provide the physician with feedback regarding whether electrical energy is currently deliverable to the ablation electrode. Further, or instead, the foot pedal can remain depressible throughout a procedure and selectively controlling delivery of electrical energy to the ablation electrode can include ignoring the signal from the foot pedal until such time that energy can be safely delivered to the treatment site through the ablation electrode.

As an additional or alternative example, the user interface can include a button (e.g., a button implemented as hardware, software, or a combination thereof) to initiate energy delivery. In such instances, selectively controlling delivery of electrical energy to the ablation electrode (block 186) can include modifying an indicator associated with or integrated with the button. That is, the indicator can be modified to indicate to the physician whether the button is currently enabled or disabled. As a more specific example, a light source can be associated with (e.g., integrated into) a button and one or more attributes of the light source can be modified according to a state of the selective control. The one or more attributes of the light source can be any one or more of various different attributes perceptible by a physician during a treatment and, thus, by way of example, can include intensity, color, and combinations thereof.

In certain applications, the physician can receive an alert (e.g., a visual alert, an audible alert, a haptic alert, or combinations thereof) of whether the user interface is enabled or disabled at a given time. Thus, continuing with this example, the physician can receive an alert when the state of the user interface changes from enabled to disabled. Further, or instead, the physician can receive an alert when the state of the user interface changes from disabled to enabled. As a more specific example, the step at block 186 of selectively controlling delivery of electrical energy to the ablation electrode can include displaying visual indicia on a graphical user interface (e.g., the catheter interface unit 114 in FIG. 1). The visual indicia can include, among other things, an indication of a time remaining until the user interface will change from a disabled state to an enabled state.

Although the steps of the method 180 are discussed and/or illustrated in a particular order, the method 180 shown in FIG. 8 is not so limited. In other implementations, the method 180 can be performed in a different order. In these and other implementations, any of the steps of the method 180 can be performed before, during, and/or after any of the other steps of the method 180. Moreover, a person of ordinary skill in the relevant art will readily recognize that the illustrated method 180 can be altered and still remain within these and other implementations of the present technology. For example, one or more steps of the method 180 illustrated in FIG. 8 can be omitted and/or repeated in some implementations.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application-specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Implementations disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same.

The method steps of the implementations described herein are intended to include any suitable method of causing such method steps to be performed, consistent with the patentability of the following claims, unless a different meaning is expressly provided or otherwise clear from the context. So, for example, performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular implementations have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

C. Additional Examples

Several aspects of the present technology are set forth in the following examples.

1. A system, comprising:
 a catheter including a shaft and an ablation electrode, the ablation electrode coupled to the shaft and positionable in an anatomic structure of a patient;
 one or more return electrodes in electrical communication with the ablation electrode, the one or more return electrodes positionable on a skin surface of the patient; and
 a controller in electrical communication with the ablation electrode and the one or more return electrodes, the controller including a non-transitory, computer-readable storage medium storing computer-executable instructions that, when executed, cause the controller to
  receive a first signal indicative of electrical energy delivered to a return electrode of the one or more return electrodes;
  determine an energy index of the return electrode of the one or more return electrodes, the energy index based, at least in part, on the first signal received in a current time-step and in one or more time-steps preceding the current time-step; and
  based, at least in part, on the energy index associated with the return electrode of the one or more return electrodes, selectively control delivery of electrical energy to the ablation electrode.

2. The system of example 1 wherein determining the energy index of the return electrode of the one or more return electrodes is based, at least in part, on the first signal received over a temporal window having a predetermined duration.

3. The system of example 2 wherein the energy index is based, at least in part, on a nonlinear function of current over the temporal window.

4. The system of example 3 wherein the energy index is based, at least in part, on a weighted sum of the nonlinear function of current over the temporal window.

5. The system as in any of examples 1-4 wherein the energy index is based, at least in part, on a heating factor of the return electrode of the one or more return electrodes.

6. The system as in any of examples 1-5 wherein selectively controlling delivery of electrical energy to the ablation electrode is based, at least in part, on a comparison of the energy index of the return electrode of the one or more return electrodes to a predetermined threshold.

7. The system of example 6 wherein the predetermined threshold is 30 amperes$^2$ over 60 seconds.

8. The system as in any of examples 1, 6, and 7 wherein, when executed, the computer-executable instructions further cause the controller to receive the predetermined threshold from a user input device.

9. The system as in any of examples 1-8 wherein, when executed, the computer-executable instructions further cause the controller to receive a second signal indicative of a request for electrical energy to the ablation electrode, and wherein selectively controlling delivery of electrical energy to the ablation electrode is further based, at least in part, on the second signal indicative of the request for the electrical energy to the ablation electrode.

10. The system of example 9 wherein the request for the electrical energy to the ablation electrode includes a maximum current and a duration.

11. The system of example 10 wherein the maximum current of the requested electrical energy to the ablation electrode corresponds to a current greater than about zero amperes and less than about 1 ampere in the return electrode of the one or more return electrodes.

12. The system as in any one of examples 9-11 wherein selectively controlling delivery of the electrical energy to the ablation electrode includes determining a projected increase of the energy index of the return electrode of the one or more return electrodes to account for the requested electrical energy, and wherein, when executed, the computer-executable instructions further cause the controller to enable delivery of the requested electrical energy to the ablation electrode to form a lesion in the anatomic structure when a combination of the energy index of the return electrode of the one or more return electrodes and the projected increase of the energy index of the return electrode of the one or more return electrodes is below a predetermined threshold.

13. The system of example 12 wherein the combination of the energy index of the return electrode of the one or more return electrodes and the projected increase of the energy index is a weighted sum or an unweighted sum of the energy index of the return electrode of the one or more return electrodes and the projected increase of the energy index.

14. The system of example 13 wherein the combination of the energy index of the return electrode of the one or more return electrodes and the projected increase of the energy index is a nonlinear combination of the energy index of the return electrode of the one or more return electrodes and the projected increase of the energy index.

15. The system as in any one of examples 1-14 wherein the one or more return electrodes includes a plurality of return electrodes and the controller further includes circuitry through which the electrical energy is distributed to the plurality of return electrodes.

16. The system of example 15 wherein receiving the first signal indicative of electrical energy in the return electrode of the one or more return electrodes includes selecting the first signal from a plurality of signals, and wherein each signal of the plurality of signals is indicative of current in a respective return electrode of the plurality of return electrodes.

17. The system of example 16 wherein selectively controlling delivery of the electrical energy to the ablation electrode is based, at least in part, on an estimate of a distribution of the requested electrical energy among the plurality of return electrodes.

18. The system of example 17 wherein the estimate of the distribution of the requested electrical energy is based, at least in part, on a distribution of electrical energy associated with at least one time-step preceding the current time-step.

19. The system of example 17 wherein the estimate of the distribution of the requested electrical energy is an equal distribution among the plurality of return electrodes.

20. The system as in any one of examples 1-19, wherein, when executed, the computer-executable instructions further cause the controller to interrupt delivery of electrical energy to the ablation electrode based, at least in part, on the energy index of the return electrode of the one or more return electrodes as the electrical energy is delivered to the ablation electrode.

21. The system as in any of examples 1-20, further comprising a graphical user interface in electrical communication with the controller, wherein the graphical user interface is associated with the ablation electrode, and wherein selectively controlling delivery of electrical energy to the ablation electrode includes selectively enabling the graphical user interface associated with the ablation electrode.

22. The system of example 21 wherein selectively enabling the graphical user interface associated with the ablation electrode includes selectively enabling one or more of a button, a foot pedal, or a touch screen associated with the ablation electrode.

23. The system as in any one of examples 1-22, further comprising a graphical user interface in electrical communication with the controller, wherein selectively controlling delivery of the electrical energy to the ablation electrode includes displaying visual indicia on the graphical user interface, the visual indicia indicative of a state of the selectively controlled delivery of the electrical energy to the ablation electrode.

24. A method of controlling lesion formation by an ablation electrode disposed in an anatomic structure of a patient, the method comprising:
receiving a first signal indicative of electrical energy delivered to a return electrode in electrical communication with the ablation electrode;
determining an energy index of the return electrode, the energy index based, at least in part, on the first signal received in a current time-step and in one or more time-steps preceding the current time-step; and
based, at least in part, on the energy index associated with the return electrode, selectively controlling delivery of electrical energy to the ablation electrode.

25. The method of example 24 wherein determining the energy index of the return electrode is based, at least in part, on the first signal received over a temporal window having a predetermined duration.

26. The method of example 25 wherein the energy index is based, at least in part, on a nonlinear function of current over the temporal window.

27. The method of example 26 wherein the energy index is based, at least in part, on a weighted sum of the nonlinear function of current over the temporal window.

28. The method as in any one of examples 24-27 wherein the energy index is based, at least in part, on a heating factor of the return electrode.

29. The method as in any one of examples 24-28 wherein selectively controlling delivery of electrical energy to the ablation electrode is based, at least in part, on a comparison of the energy index of the return electrode to a predetermined threshold.

30. The method of example 29 wherein the predetermined threshold is 30 amperes$^2$ over 60 seconds.

31. The method as in any one of examples 24, 29, and 30, further comprising receiving the predetermined threshold from a user input device.

32. The method as in any one of examples 24-31, further comprising receiving a second signal indicative of a request for electrical energy to the ablation electrode, and wherein selectively controlling delivery of electrical energy to the ablation electrode is further based, at least in part, on the second signal indicative of the request for the electrical energy to the ablation electrode.

33. The method of example 32 wherein the request for the electrical energy to the ablation electrode includes a maximum current and a duration.

34. The method of example 33 wherein the maximum current of the requested electrical energy to the ablation electrode corresponds to a current greater than about zero amperes and less than about 1 ampere in the return electrode.

35. The method as in any one of examples 32-34 wherein selectively controlling delivery of the electrical energy to the ablation electrode includes determining a projected increase of the energy index of the return electrode to account for the requested electrical energy, and wherein the method further comprises enabling delivery of the requested electrical energy to the ablation electrode to form a lesion in the anatomic structure when a combination of the energy index of the return electrode and the projected increase of the energy index of the return electrode is below a predetermined threshold.

36. The method of example 35 wherein the combination of the energy index of the return electrode and the projected increase of the energy index is a weighted sum or an unweighted sum of the energy index of the return electrode and the projected increase of the energy index.

37. The method of example 36 wherein the combination of the energy index of the return electrode and the projected increase of the energy index is a nonlinear combination of the energy index of the return electrode and the projected increase of the energy index.

38. The method as in any one of examples 32-37 wherein receiving the first signal indicative of electrical energy in the return electrode includes selecting the first signal from a plurality of signals, and wherein each signal of the plurality of signals is indicative of current in a respective return electrode of a plurality of return electrodes.

39. The method of example 38 wherein selectively controlling delivery of the electrical energy to the ablation electrode is based, at least in part, on an estimate of a distribution of the requested electrical energy among the plurality of return electrodes.

40. The method of example 39 wherein the estimate of the distribution of the requested electrical energy is based, at least in part, on a distribution of electrical energy associated with at least one time-step preceding the current time-step.

41. The method of example 39 wherein the estimate of the distribution of the requested electrical energy is an equal distribution among the plurality of return electrodes.

42. The method as in any one of examples 24-41, further comprising interrupting delivery of electrical energy to the ablation electrode based, at least in part, on the energy index of the return electrode as the electrical energy is delivered to the ablation electrode.

43. The method as in any one of examples 24-42 wherein selectively controlling delivery of electrical energy to the ablation electrode includes selectively enabling a user interface associated with the ablation electrode.

44. The method of example 43 wherein selectively enabling the user interface associated with the ablation electrode includes selectively enabling one or more of a button, a foot pedal, or a touch screen associated with the ablation electrode.

45. The method as in any one of examples 24-44 wherein selectively controlling delivery of the electrical energy to the ablation electrode includes displaying visual indicia on a graphical user interface, the visual indicia indicative of a state of the selectively controlled delivery of the electrical energy to the ablation electrode.

46. A non-transitory, computer-readable storage medium having stored thereon computer-executable instructions for causing one or more processors to carry out a method of controlling lesion formation by an ablation electrode disposed in an anatomic structure of a patient, the method comprising:
receiving a first signal indicative of electrical energy delivered to a return electrode in electrical communication with the ablation electrode;
determining an energy index of the return electrode, the energy index based, at least in part, on the first signal received in a current time-step and in one or more time-steps preceding the current time-step; and based, at least in part, on the energy index associated with the return electrode, selectively controlling delivery of electrical energy to the ablation electrode.

47. The non-transitory, computer readable storage medium of example 46 wherein determining the energy index of the return electrode is based, at least in part, on the first signal received over a temporal window having a predetermined duration.

48. The non-transitory, computer readable storage medium of example 47 wherein the energy index is based, at least in part, on a nonlinear function of current over the temporal window.

49. The non-transitory, computer readable storage medium of example 48 wherein the energy index is based, at least in part, on a weighted sum of the nonlinear function of current over the temporal window.

50. The non-transitory, computer readable storage medium as in any one of examples 46-49 wherein the energy index is based, at least in part, on a heating factor of the return electrode.

51. The non-transitory, computer readable storage medium as in any one of examples 46-50 wherein selectively controlling delivery of electrical energy to the ablation electrode is based, at least in part, on a comparison of the energy index of the return electrode to a predetermined threshold.

52. The non-transitory, computer readable storage medium of example 51 wherein the predetermined threshold is 30 amperes$^2$ over 60 seconds.

53. The non-transitory, computer readable storage medium as in any one of examples 46, 51, and 52 wherein the method further comprises receiving the predetermined threshold from a user input device.

54. The non-transitory, computer readable storage medium as in any one of examples 46-53 wherein the method further comprises receiving a second signal indicative of a request for electrical energy to the ablation electrode, and wherein selectively controlling delivery of electrical energy to the ablation electrode is further based, at least in part, on the second signal indicative of the request for the electrical energy to the ablation electrode.

55. The non-transitory, computer readable storage medium of example 54 wherein the request for the electrical energy to the ablation electrode includes a maximum current and a duration.

56. The non-transitory, computer readable storage medium of example 55 wherein the maximum current of the requested electrical energy to the ablation electrode corresponds to a current greater than about zero amperes and less than about one ampere in the return electrode.

57. The non-transitory, computer readable storage medium as in any one of examples 54-56 wherein selectively controlling delivery of the electrical energy to the ablation electrode includes determining a projected increase of the energy index of the return electrode to account for the requested electrical energy, and wherein the method further comprises enabling delivery of the requested electrical energy to the ablation electrode to form a lesion in the anatomic structure when a combination of the energy index of the return electrode and the projected increase of the energy index of the return electrode is below a predetermined threshold.

58. The non-transitory, computer readable storage medium of example 57 wherein the combination of the energy index of the return electrode and the projected increase of the energy index is a weighted sum or an unweighted sum of the energy index of the return electrode and the projected increase of the energy index.

59. The non-transitory, computer readable storage medium of example 58 wherein the combination of the energy index of the return electrode and the projected increase of the energy index is a nonlinear combination of the energy index of the return electrode and the projected increase of the energy index.

60. The non-transitory, computer readable storage medium as in any one of examples 54-59 wherein receiving the first signal indicative of electrical energy in the return electrode includes selecting the first signal from a plurality of signals, and wherein each signal of the plurality of signals is indicative of current in a respective return electrode of a plurality of return electrodes.

61. The non-transitory, computer readable storage medium of example 60 wherein selectively controlling delivery of the electrical energy to the ablation electrode is based, at least in part, on an estimate of a distribution of the requested electrical energy among the plurality of return electrodes.

62. The non-transitory, computer readable storage medium of example 61 wherein the estimate of the distribution of the requested electrical energy is based, at least in part, on a distribution of electrical energy associated with at least one time-step preceding the current time-step.

63. The non-transitory, computer readable storage medium of example 61 wherein the estimate of the distribution of the requested electrical energy is an equal distribution among the plurality of return electrodes.

64. The non-transitory, computer readable storage medium as in any one of examples 46-63 wherein the method further comprises interrupting delivery of electrical energy to the ablation electrode based, at least in part, on the energy index of the return electrode as the electrical energy is delivered to the ablation electrode.

65. The non-transitory, computer readable storage medium as in any one of examples 46-64 wherein selectively controlling delivery of electrical energy to the ablation electrode includes selectively enabling a user interface associated with the ablation electrode.

66. The non-transitory, computer readable storage medium of example 65 wherein selectively enabling the user interface associated with the ablation electrode includes selectively enabling one or more of a button, a foot pedal, or a touch screen associated with the ablation electrode.

67. The non-transitory, computer readable storage medium as in any one of examples 46-66 wherein selectively controlling delivery of the electrical energy to the ablation electrode includes displaying visual indicia on a graphical user interface, the visual indicia indicative of a state of the selectively controlled delivery of the electrical energy to the ablation electrode.

CONCLUSION

The above detailed descriptions of implementations of the present technology are not intended to be exhaustive or to limit the technology to the precise form disclosed above. Although specific implementations of, and examples for, the technology are described above for illustrative purposes, various equivalent modifications are possible within the scope of the technology, as those skilled in the relevant art will recognize. For example, while steps are presented in a given order, alternative implementations can perform steps in a different order. Furthermore, the various implementations described herein can also be combined to provide further implementations.

From the foregoing, it will be appreciated that specific implementations of the present technology have been described herein for purposes of illustration, but well-known structures and functions have not been shown or described in detail to avoid unnecessarily obscuring the description of the implementations of the present technology. Where the context permits, singular or plural terms can also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms can also include the plural or singular term, respectively. Additionally, the terms "comprising," "including," "having" and "with" are used throughout to mean including at least the recited feature(s) such that any greater number of the same feature and/or additional types of other features are not precluded. To the extent any materials incorporated herein by reference conflict with the present disclosure, the present disclosure controls.

From the foregoing, it will also be appreciated that various modifications can be made without deviating from the technology. For example, various components of the technology can be further divided into subcomponents, or that various components and functions of the technology can be combined and/or integrated. Furthermore, although advantages associated with certain implementations of the present technology have been described in the context of those implementations, other implementations can also exhibit such advantages, and not all implementations need necessarily exhibit such advantages to fall within the scope of the present technology.

What is claimed is:

1. A system for ablating a tissue of a patient, comprising:
   a catheter including a shaft and an ablation electrode, the ablation electrode coupled to the shaft and positionable in an anatomic structure associated with the tissue of the patient;
   a return electrode in electrical communication with the ablation electrode, the return electrode positionable on a skin surface of the patient; and
   a controller in electrical communication with the ablation electrode and the return electrode, the controller including a non-transitory, computer-readable storage medium storing computer-executable instructions that, when executed, is configured to cause the controller to:
      receive a first signal indicative of a measure of electrical energy delivered to the return electrode during a first treatment time period;
      receive a second signal indicative of a request for a second amount and/or duration of electrical energy to be delivered to the ablation electrode during a second treatment time period, wherein the second treatment time period is a future time period subsequent to the first treatment time period;
      determine a projected energy index of the return electrode for the second treatment time period, the projected energy index based on the measure of electrical energy delivered to the return electrode during the first treatment time period and the second amount and/or duration of electrical energy requested by the second signal; and
      selectively enable delivery of the second amount and/or duration of electrical energy to the ablation electrode for the second treatment time period, based on a comparison of the projected energy index of the return electrode to a predetermined threshold.

2. The system of claim 1 wherein determining the projected energy index of the return electrode is based on the first signal received over a temporal window having a predetermined duration.

3. The system of claim 2 wherein the projected energy index is based on a nonlinear function of current over the temporal window.

4. The system of claim 3 wherein the projected energy index is based on a weighted sum of the nonlinear function of current over the temporal window.

5. The system of claim 4 wherein the projected energy index is based on a heating factor of the return electrode.

6. The system of claim 1 wherein the predetermined threshold is 30 amperes$^2$ over 60 seconds.

7. The system of claim 1 wherein, when executed, the computer-executable instructions further cause the controller to receive the predetermined threshold from a user input device.

8. The system of claim 1 wherein the second signal includes a maximum current and the duration of electrical energy.

9. The system of claim 8 wherein the maximum current of the requested second amount and/or duration of electrical energy to the ablation electrode corresponds to a current greater than about zero amperes and less than 1 ampere in the return electrode of the one or more return electrodes.

10. The system of claim 1 wherein determining the projected energy index is based on a weighted sum or an unweighted sum of an energy index of the return electrode for at least a portion of the first treatment time period and a projected increase of the energy index of the return electrode for at least a portion of the second treatment time period.

11. The system of claim 1 wherein determining the projected energy index is based on a nonlinear combination of an energy index of the return electrode for at least a portion of the first treatment time period and a projected increase of the energy index of the return electrode for at least a portion of the second treatment time period.

12. The system of claim 1, wherein determining the projected energy index is based on an estimate of a distribution of the requested electrical energy among the plurality of return electrodes.

13. The system of claim 12 wherein the estimate of the distribution of the requested second amount and/or duration of electrical energy is based on a distribution of electrical energy associated with at least one treatment time period preceding the first treatment time period.

14. The system of claim 12 wherein the estimate of the distribution of the requested second amount and/or duration of electrical energy is an equal distribution among the plurality of return electrodes.

15. The system of claim 1, wherein, when executed, the computer-executable instructions further cause the controller to interrupt delivery of the second amount and/or duration of electrical energy to the ablation electrode based on the projected energy index of the return electrode of the as the second amount and/or duration of electrical energy is delivered to the ablation electrode.

16. The system of claim 1, further comprising a graphical user interface in electrical communication with the controller, wherein the graphical user interface is associated with the ablation electrode, and wherein selectively enabling delivery of the second amount and/or duration of electrical energy to the ablation electrode includes selectively enabling the graphical user interface associated with the ablation electrode.

17. The system of claim 1, further comprising a graphical user interface in electrical communication with the controller, wherein selectively enabling delivery of the second amount and/or duration of electrical energy to the ablation electrode includes displaying visual indicia on the graphical user interface, the visual indicia indicative of a state of the selectively controlled delivery of the the second amount and/or duration of electrical energy to the ablation electrode.

18. A system for ablating a tissue of a patient, comprising:
a catheter including a shaft and an ablation electrode, the ablation electrode coupled to the shaft and positionable in an anatomic structure associated with the tissue of the patient;
a plurality of return electrodes in electrical communication with the ablation electrode, each of the plurality of return electrodes positionable on a skin surface of the patient; and
a controller in electrical communication with the ablation electrode and the plurality of return electrodes, the controller including circuitry configured to control distribution of an electrical energy among the plurality of return electrodes, and a non-transitory, computer-readable storage medium storing computer-executable instructions that, when executed, cause the controller to
receive a first signal indicative of a measure of electrical energy delivered to a given return electrode of the plurality of return electrodes during a first treatment time period;
receive a second signal indicative of a request for a second amount and/or duration of electrical energy to be delivered to the ablation electrode during a second treatment time period, wherein the second treatment time period is a future time period subsequent to the first treatment time period;
determine a projected energy index of the given return electrode of the plurality of return electrodes for the second treatment time period based on the measure of electrical energy delivered to the given return electrode of the plurality of return electrodes during the first treatment time period and the second amount and/or duration of electrical energy requested by the second signal;
selectively enable delivery of the second amount and/or duration of electrical energy to the ablation electrode for the second treatment time period, based on a comparison of the projected energy index of the given return electrode of the plurality of return electrodes to a predetermined threshold.

19. The system of claim 18 wherein the controller is configured to receive the first signal by selecting the first signal from a plurality of signals, and wherein each signal of the plurality of signals is indicative of current in a respective return electrode of the plurality of return electrodes.

20. The system of claim 18, wherein the circuitry is coupled to at least two of the return electrodes of the plurality return electrodes, and the controller is configured to control the distribution of the electrical energy among the at least two return electrodes of the plurality return electrodes through the circuitry.

* * * * *